United States Patent
Shih et al.

(10) Patent No.: US 10,194,886 B2
(45) Date of Patent: Feb. 5, 2019

(54) ACOUSTIC WAVE INTRAOCULAR PRESSURE DETECTING DEVICE AND METHOD THEREOF

(71) Applicant: National Taiwan University, Taipei (TW)

(72) Inventors: Wen-Pin Shih, Taipei (TW); Po-Jen Shih, Kaohsiung (TW); Jia-Yush Yen, Taipei (TW); I-Jong Wang, Taipei (TW)

(73) Assignee: National Taiwan University (TW)

( * ) Notice: Subject to any disclaimer, the term of this patent is extended or adjusted under 35 U.S.C. 154(b) by 466 days.

(21) Appl. No.: 14/972,508

(22) Filed: Dec. 17, 2015

(65) Prior Publication Data
US 2016/0174933 A1 Jun. 23, 2016

(30) Foreign Application Priority Data
Dec. 18, 2014 (TW) .............................. 103144342 A

(51) Int. Cl.
*A61B 5/00* (2006.01)
*A61B 8/10* (2006.01)
*A61B 8/08* (2006.01)
*A61B 5/16* (2006.01)

(52) U.S. Cl.
CPC .............. *A61B 8/10* (2013.01); *A61B 8/5223* (2013.01); *A61B 5/165* (2013.01)

(58) Field of Classification Search
CPC .............. A61B 3/16; A61B 3/165; A61B 8/10
See application file for complete search history.

(56) References Cited

U.S. PATENT DOCUMENTS

| | | | | |
|---|---|---|---|---|
| 6,595,920 B2 * | 7/2003 | Walton | ................... | A61B 3/165 600/401 |
| 6,673,014 B2 * | 1/2004 | Badehi | ................... | A61B 3/165 600/398 |
| 7,419,470 B2 * | 9/2008 | Uchiyama | ................ | A61B 8/10 600/437 |
| 8,172,769 B2 * | 5/2012 | Lenhardt | ................ | A61B 5/031 600/561 |
| 9,462,947 B2 * | 10/2016 | Kontiola | ................ | A61B 3/165 |
| 2004/0097799 A1 | 5/2004 | Uchiyama et al. | | |
| 2007/0123796 A1 | 5/2007 | Lenhardt et al. | | |

FOREIGN PATENT DOCUMENTS

CN    1511009 A    7/2004

* cited by examiner

*Primary Examiner* — Max Hindenburg
(74) *Attorney, Agent, or Firm* — Levine Bagade Han LLP

(57) ABSTRACT

The present invention provides an acoustic wave intraocular pressure detecting device and a method thereof, which uses a driver to generate a vibration wave on the skin or bones. The energy of the vibration wave is transmitted to the orbital bones via the skin and the skeletons. A standing wave of the basin effect is generated on the eyeball inside the orbital bones. The standing wave vibrates the eyeball or the cornea to generate an acoustic wave signal with a resonance frequency. The eyeball or the cornea emits the acoustic wave outwardly. A receiver receives the acoustic wave and converts the acoustic wave into an intraocular pressure (IOP) value.

13 Claims, 5 Drawing Sheets

ACOUSTIC WAVE INTRAOCULAR PRESSURE DETECTING DEVICE AND METHOD THEREOF

BACKGROUND OF THE INVENTION

1. Field of the Invention

The present invention relates to an intraocular pressure detecting device and method thereof, especially a non-invasive intraocular pressure detecting device and method thereof by acoustic wave theorem.

2. Description of the Prior Art

Most of the conventional intra-ocular pressure (IOP) detecting device, such as an invasive device, a handheld device, or a desktop device, detect IOP by way of invasion or contact, such as implanting a detecting device on the surface of the eyeball, using a probe to press on the cornea, or blowing air to the eyeball. During the detection process, sometimes anesthesia drops would be applied to the eyeball. As a result, subjects may feel uncomfortable or shed tears as a result of contact. In addition to causing subjects' discomfort, it also increases the inconvenience of detection.

Consequently, in recent year, non-contact detection methods have been developed, such as emitting light into human eyes for detecting the IOP by measuring the vibration on the surface of the eyeball subjected by air puff or oscillators. But the process may cause the subject's discomfort.

Furthermore, in terms of time needed for detection, in general, the subject should be observed in a hospital. The medical staff would take measurement for the subject once in a while. As a result, this may cause the subject's discomfort. For the potential glaucoma subject, high IOP happens at early morning and late evening. Sometimes the subject cannot detect IOP as frequently as possible, and that causes delays in medical treatment.

SUMMARY OF THE INVENTION

In view of the above problems, in one aspect, the present invention provides a non-contact and a non-invasive acoustic wave intraocular pressure detecting device, comprising a driver and a receiver. The low energy driver is configured to generate a vibration wave, with the vibration wave transmitted to orbital bones via skin and bones (Temporal, Sphenoid, Zygomatic, Frontal, or Maxilla bones) to form the basin effect of the eyeball inside the orbital bones, wherein the standing wave of the basin effect vibrates the eyeball or cornea to generate an acoustic wave signal with a resonance frequency and emit such acoustic wave signal outwardly. The receiver is configured to receive the acoustic wave signal and convert the acoustic wave signal into an intraocular pressure value.

The vibration wave is a sinusoidal wave signal or a pulse signal, having the frequency of about 0~1.0 kHz. The vibration wave energy is greater than 1.23 mW. The resonance frequency and the intraocular pressure value has a mathematical relationship:

$$f_n = \frac{1}{2\pi} \sqrt{\frac{\frac{(E+T) \cdot t^3}{12(1-v^2)} \frac{n^3(n+1)^3}{R^4} + \frac{T \cdot t \cdot n^2(n+1)^2}{R^2}}{[(n+1)\rho_i + n \cdot \rho_o]R + n(n+1)\rho \cdot t}},$$

wherein E is average Young's modulus of sclera, T is tension of sclera, t is average thickness of sclera, R is average radius of eyeball, v is Poisson's ratio, $\rho_i$ is average density of inner eyeball, $\rho$ is average density of sclera, $\rho_o$ is air density, and n is modal order number. And $T=T_0 + IOP \cdot R/2t$, wherein the IOP is the intraocular pressure value, $T_0$ is an initial tension value that the eyeball is under a balanced state of having the same inner pressure and outer pressure.

In another aspect, the present invention provides an acoustic wave intraocular pressure detecting method. The method is comprised of the following steps: (S1) using a low energy driver to generate a vibration wave to skin or bones, the vibration wave is transmitted to orbital bones via skin and bones (Temporal, Sphenoid, Zygomatic, Frontal, or Maxilla bones) to form the basin effect of the eyeball inside the orbital bones, wherein the standing wave vibrates the eyeball or cornea to generate an acoustic wave signal with a resonance frequency and emit such acoustic wave signal outwardly; (S2) using a receiver to receive the acoustic wave signal and convert the acoustic wave signal into an intraocular pressure value; and (S3) sending the intraocular pressure value to a database for comparison.

In comparison to the prior art, the acoustic wave intraocular pressure detecting device and method thereof provided in this application transmits the vibration wave to orbital bones via skin or skeletons, using the natural structure of orbital bones and eyeball to form a standing wave of the basin effect. The standing wave vibrates the eyeball or cornea to generate an acoustic wave signal with a resonance frequency, and then the acoustic wave signal received is converted into an intraocular pressure value. Accordingly, using the acoustic wave theorem and the basin effect, the intraocular pressure can be immediately detected and the subject would not feel any discomfort during the detection process.

DETAILED DESCRIPTION OF THE PREFERRED EMBODIMENT

Figure 1:
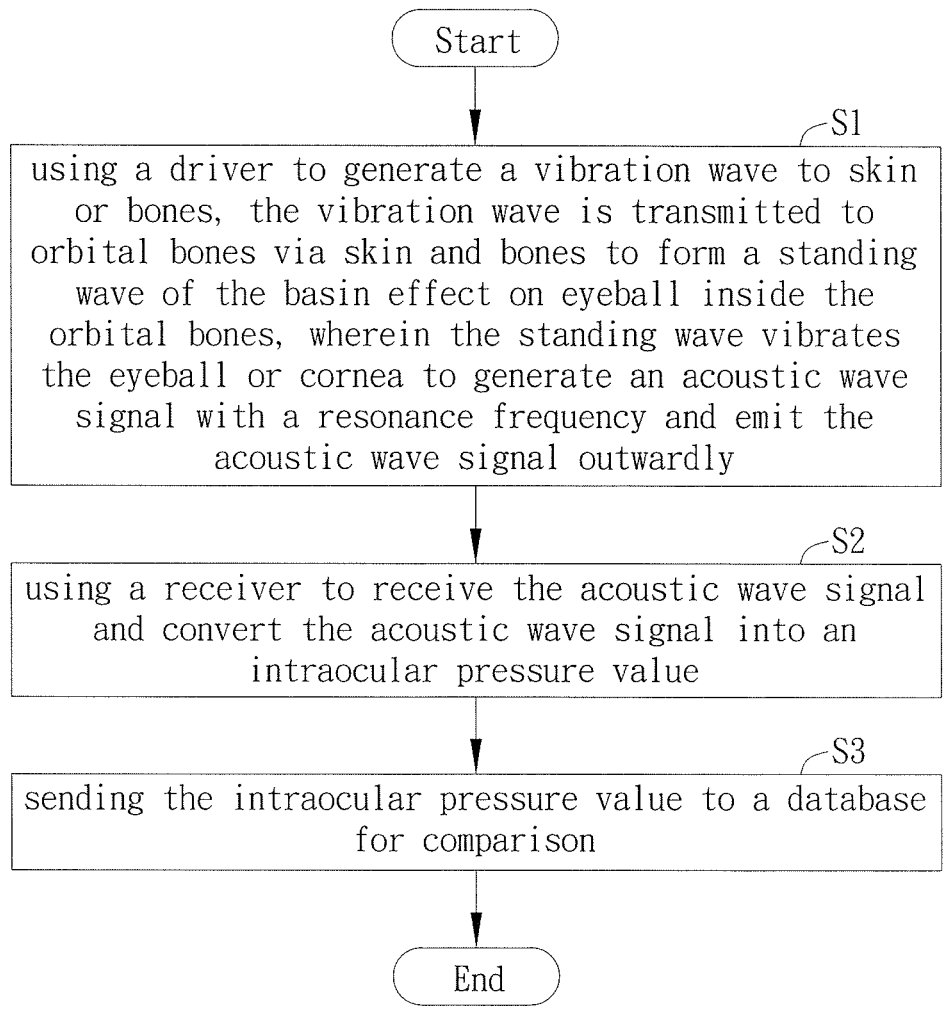
FIG. 1 is a flow chart in an embodiment.
Figure 2A:
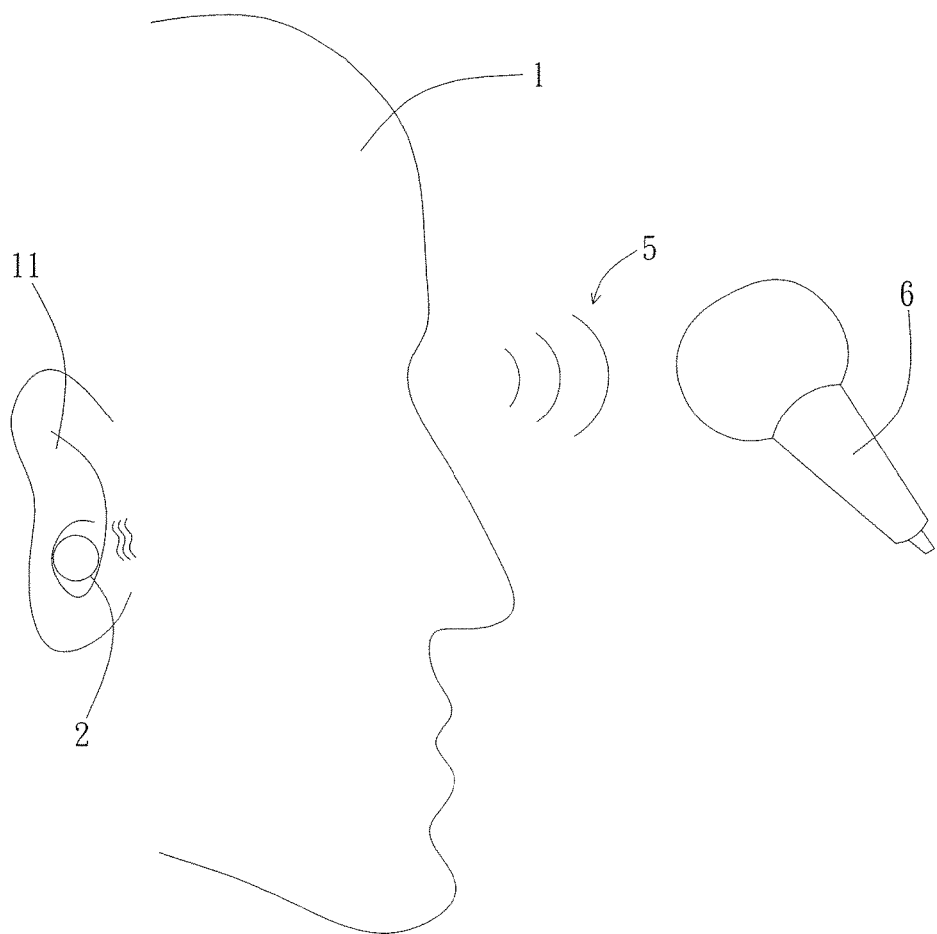
FIGS. 2A-2D are schematic diagrams in an embodiment.
Figure 2B:
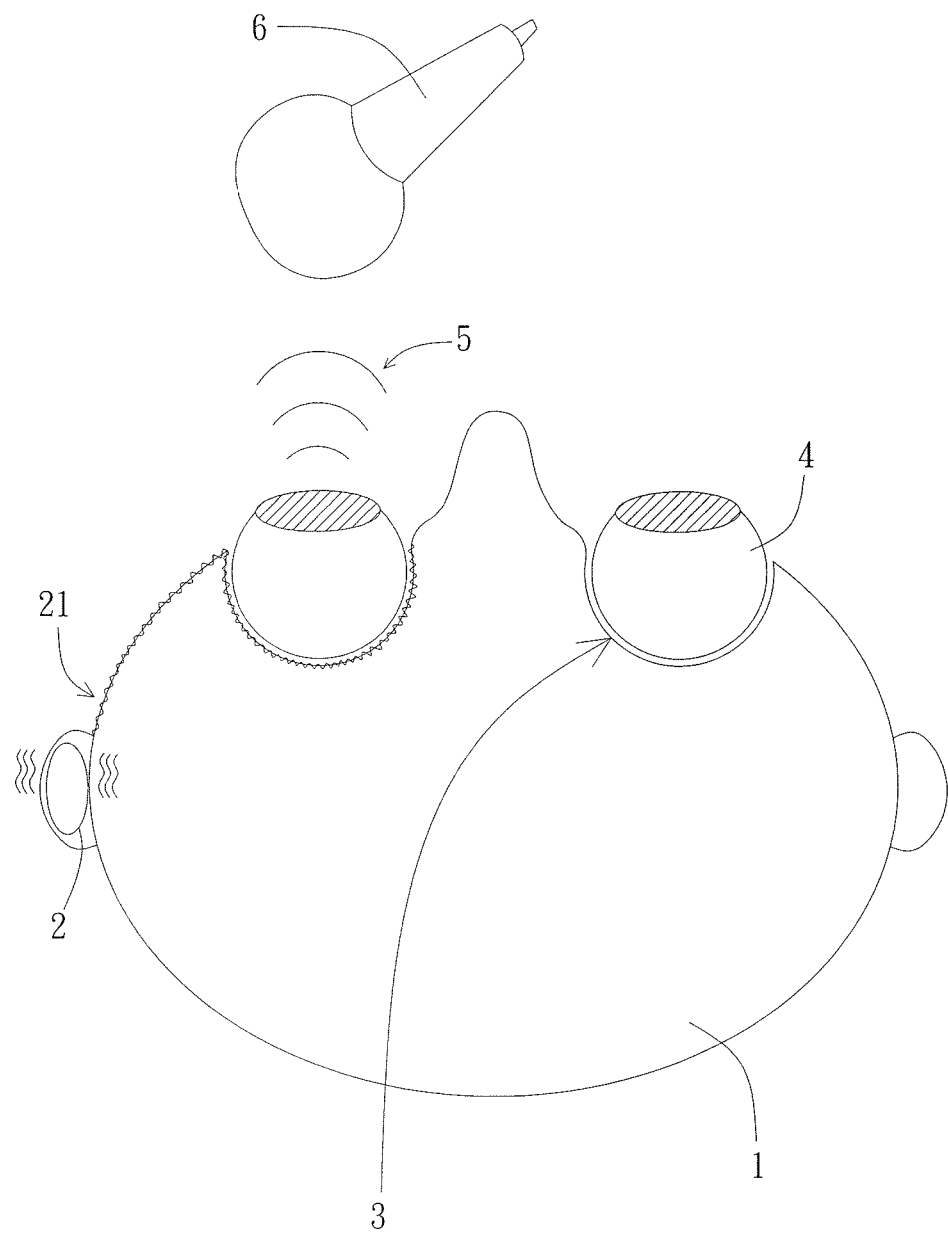

Please refer to FIG. 1, FIG. 2A and FIG. 2B. As shown in FIG. 2A and FIG. 2B, step (S1): using a driver to generate a vibration wave to skin or bones, the vibration wave is transmitted to orbital bones via skin and bones (Temporal, Sphenoid, and Zygomatic bones) to form the basin effect of the eyeball inside the orbital bones, wherein the standing wave vibrates the eyeball or cornea to generate an acoustic wave signal with a resonance frequency and emit such acoustic wave signal outwardly.

As shown in FIG. 2A, an acoustic wave intraocular pressure detecting device is comprised of a driver 2 and a receiver 6. The driver 2 includes a vibrating device, but not limited thereto, as long as it can generate vibration. The driver 2 controls the frequency of the vibrating device with a microcontroller (not shown) inside the driver 2. The receiver 6 can be a microphone, a piezoelectric receiver or any other device which can receive the acoustic wave signal. In this embodiment, we set the driver 2 in the ear of subject 1. However, in other embodiment, we can also paste the driver 2 on other parts of the subject 1. The driver 2 can be formed into an earphone, a glasses, braces, or other wearable devices, but not limited thereto, as long as the driver 2 contacts skin or bones. The said other parts of subjects 1 refers to a location where the vibration wave can be transmitted to the orbital bones via skin and bones. The driver 2 generates the vibration wave to skin 11, wherein the vibration wave can be a sinusoidal wave signal, and the frequency of the sinusoidal wave is about 0~1.0 kHz, preferably about 40 Hz~400 Hz, but not limited thereto. However, the vibration wave can also be a pulse signal, with the frequency of the pulse signal about 0~1.0 kHz, and the cycle of the pulse signal about 10~20 seconds, but not limited thereto.

As shown in FIG. 2B, the vibration wave 21 is transmitted to the orbital bones 3 via skin and bones (Temporal, Sphenoid, and Zygomatic bones). Since the hardness of the orbital bones 3 is high and the eyeball 4 is located inside the orbital bones 3 and its hardness is low, accordingly, the energy converges on the eyeball 4 easily; that is, the vibration wave 21 forms the basin effect inside the eyeball 4. The standing wave vibrates the eyeball 4 or cornea to generate an acoustic wave signal 5 with a resonance frequency. The resonance frequency is obtained by the above-mentioned vibration wave with a sweep frequency (e.g. 0~1.0 kHz) or a constant pulse frequency (e.g. 10 or 20 seconds). The eyeball 4 or the cornea emits the acoustic wave signal 5 outwardly.

Figure 2C:
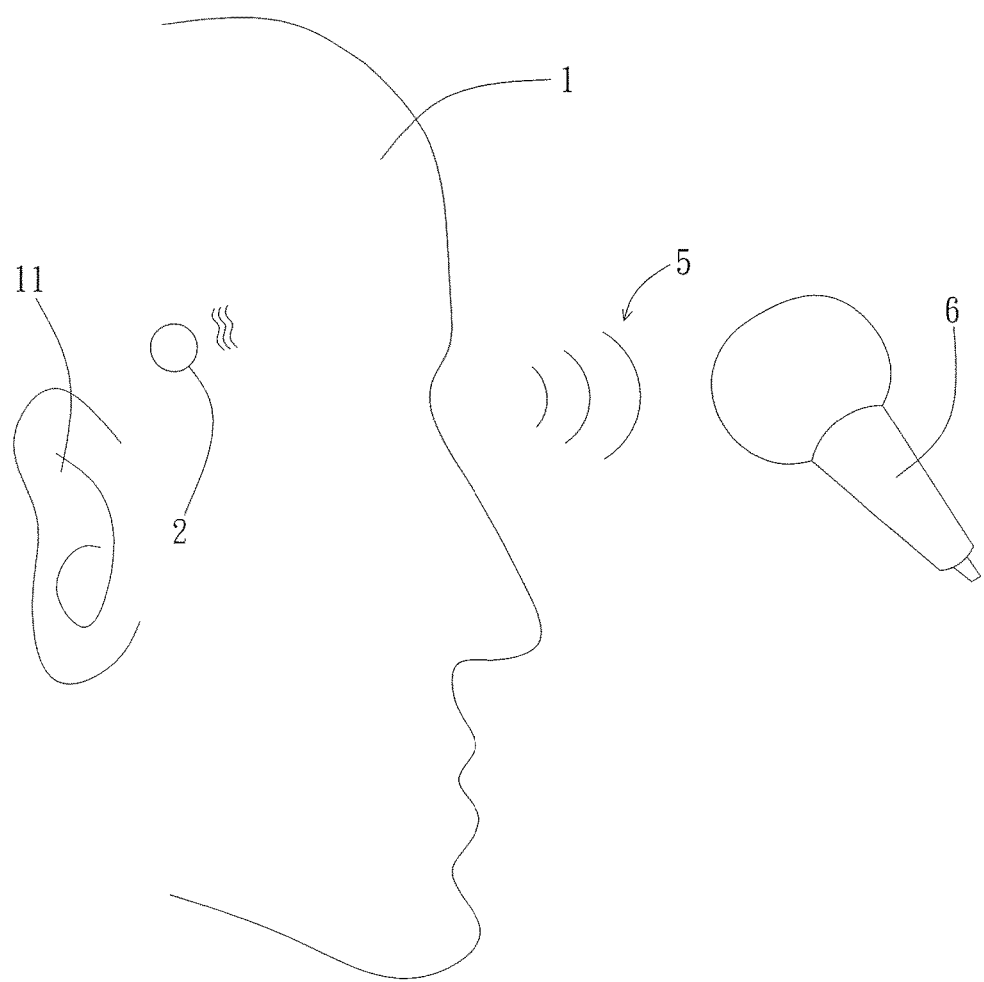

In other embodiment, as shown in FIG. 2C, the driver 2 is pasted on the subject 1's temple. Likewise, the energy of the vibration wave 21 is transmitted to the orbital bones 3 via skin and bones (Frontal, Sphenoid, and Zygomatic bones), and it forms the basin effect inside the eyeball 4. The standing wave of the basin effect vibrates the eyeball 4 or cornea to generate an acoustic wave signal 5 with a resonance frequency. Then the eyeball 4 or the cornea emits the acoustic wave signal 5 outwardly, wherein the resonance frequency is the same as the above embodiment.

It is noted that, to make the energy of the vibration wave 21 be transmitted to the orbital bones via skin and bones, and to make the eyeball or cornea vibrate to emit the acoustic wave signal, the energy is preferably greater than 1.23 mW.

Figure 2D:
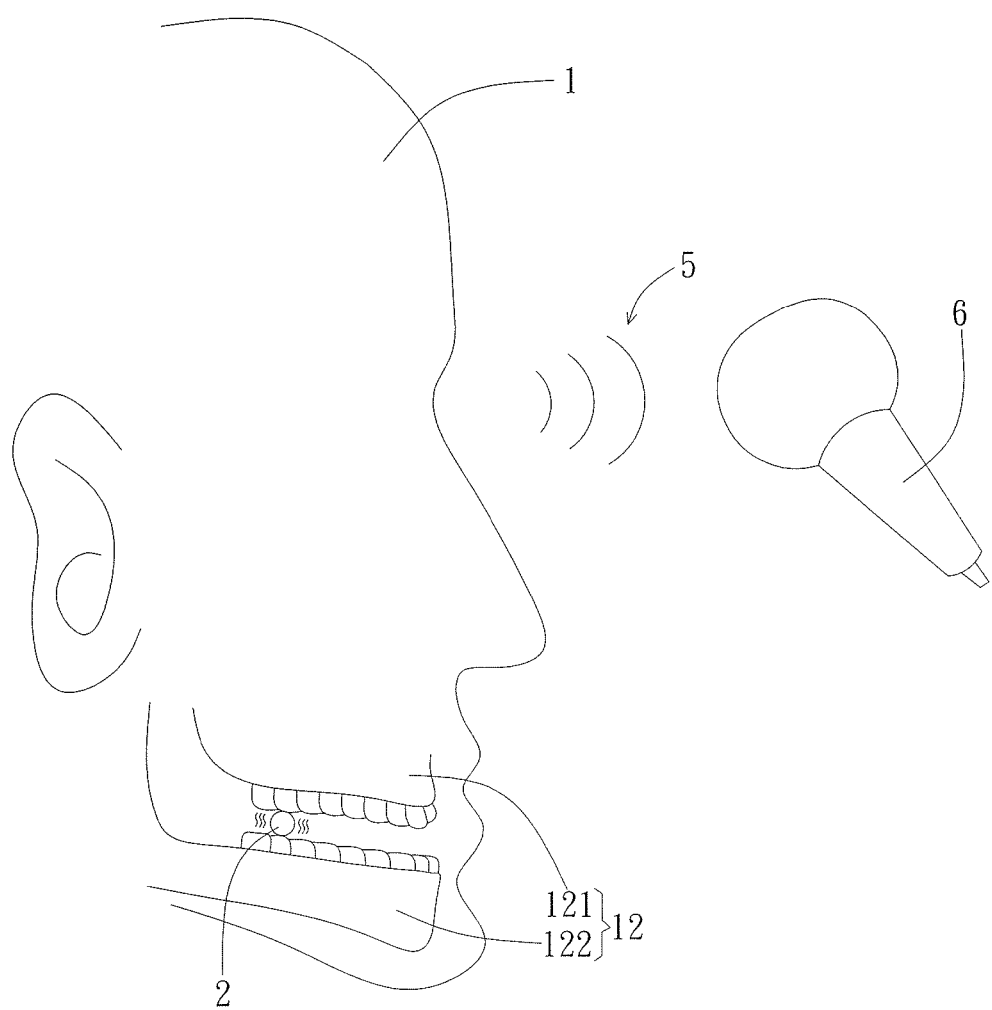

In other embodiment, as shown in FIG. 2D, the driver 2 can also be placed inside the subject 1's oral cavity. For example, the subject 1 occludes the driver 2 by teeth. Then the vibration wave from the driver 2 would be transmitted to the orbital bones through teeth, Maxilla bone, and Mandible bone 12, and form a standing wave of the basin effect inside the eyeball. However, in other embodiments, the driver 2 may be pasted directly on the top dental bone 121 of the subject 1.

The step (S2): using a receiver to receive the acoustic wave signal and convert the acoustic wave signal into an intraocular pressure value. Please refer to FIG. 2A and FIG. 2B again. Place the receiver 6 at a specific distance (e.g. 5 cm, but not limited thereto) in front of the eyeball 4 or cornea, or other position where the acoustic wave signal 5 emitted from the eyeball 4 or cornea can be received. In this embodiment, the receiver 6 is a microphone, but not limited thereto. The receiver 6 receives the acoustic wave signal 5 from the eyeball 4 or cornea, and transmits the data of the acoustic wave signal 5 to a computer (not shown). The computer then converts the resonance frequency included in the acoustic wave signal 5 into an intraocular pressure (IOP) value. Certainly, in other embodiments, the receiver 6 could include a microprocessor inside for converting the resonance frequency included in the acoustic wave signal 5.

Step (S3): sending the intraocular pressure value to a database for comparison. In this embodiment, we may set a transmission module (not shown) in the receiver 6, such as a wireless transmission module, but not limited thereto, to transmit the received IOP value to a database via the transmission module for comparison. Accordingly, the computer can determine or calculate other physical characteristics. It can also store the IOP value in the database and facilitate recording. The database may include normal IOP values, different IOP values corresponding to different diseases, and so on.

It is noted that the present invention uses the resonance frequency $f_n$, from eyeball or cornea to obtain the IOP value, wherein the resonance frequency $f_n$, and the IOP value have the following mathematical relationship:

$$f_n = \frac{1}{2\pi} \sqrt{\frac{\frac{(E+T) \cdot t^3}{12(1-v^2)} \frac{n^3(n+1)^3}{R^4} + \frac{T \cdot t \cdot n^2(n+1)^2}{R^2}}{[(n+1)\rho_i + n \cdot \rho_o]R + n(n+1)\rho \cdot t}},$$

wherein E is average Young's modulus of sclera, e.g. 0.1~2.0 MPa; t is average thickness of sclera, e.g. 0.45~0.60 mm; R is average radius of eyeball, e.g. 10~12 mm; v is Poisson's ratio, about 0.49; $\rho^i$ is average density of inner eyeball, e.g. 1000 kg/m$^3$; $\rho$ is average density of sclera, e.g. 1200~1600 kg/m$^3$; $\rho_o$ is air density, about 1.204 kg/m$^3$; n is modal order number (n=1, 2, 3 . . . ). T is tension of sclera, wherein T=T$_0$+IOP·R/2t, IOP is the intraocular pressure value, and T$_0$ is an initial tension value that the eyeball is under a balanced state (IOP=0) of having the same inner pressure and outer pressure. Substituting the above-mentioned parameters or coefficients and the detected resonance frequency into the mathematical relationship, we can obtain the IOP. It is noted that, the above parameters of eyeball structure may be different corresponding to each subject's physiological structure. They are only taken as an example here, but not limited thereto.

In comparison to the prior art, the acoustic wave intraocular pressure detecting device and method thereof provided in this application transmits the vibration wave to orbital bones via skin or skeletons, using the natural structure of orbital bones and eyeball to form a standing wave of the basin effect. The standing wave vibrates the eyeball or cornea to generate an acoustic wave signal with a resonance frequency, then the acoustic wave signal received is converted into an intraocular pressure value. Accordingly, using the acoustic wave theorem and a simple structure, intraocular pressure can be immediately detected and the subject would not feel any discomfort during the detection process.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. An acoustic wave intraocular pressure detecting device, comprising:
    a driver configured to generate a vibration wave, the vibration wave transmitted to orbital bones via skin and bones to form a standing wave of the basin effect on an eyeball inside the orbital bones, wherein the standing wave vibrates the eyeball or cornea to generate an acoustic wave signal with a resonance frequency and emit the acoustic wave signal outwardly; and
    a receiver configured to receive the acoustic wave signal when spaced by a distance from the eyeball or the cornea and convert the acoustic wave signal into an intraocular pressure value.

2. The acoustic wave intraocular pressure detecting device as claimed in claim 1, wherein the vibration wave is a sinusoidal wave signal, and the frequency of the sinusoidal wave is about 0~1.0 kHz.

3. The acoustic wave intraocular pressure detecting device as claimed in claim 1, wherein the vibration wave is a pulse signal, frequency of the pulse signal is about 0~1.0 kHz, and the cycle of the pulse signal is about 10~20 seconds.

4. The acoustic wave intraocular pressure detecting device as claimed in claim 1, wherein energy of the vibration wave is greater than 1.23 mW.

5. An acoustic wave intraocular pressure detecting device, comprising:
   a driver configured to generate a vibration wave, the vibration wave transmitted to orbital bones via skin and bones to form a standing wave of the basin effect on eyeball inside the orbital bones, wherein the standing wave vibrates the eyeball or cornea to generate an acoustic wave signal with a resonance frequency and emit the acoustic wave signal outwardly; and
   a receiver configured to receive the acoustic wave signal and convert the acoustic wave signal into an intraocular pressure value,
   wherein the resonance frequency and the intraocular pressure value has a mathematical relationship:

$$f_n = \frac{1}{2\pi} \sqrt{\frac{\frac{(E+T) \cdot t^3}{12(1-v^2)} \frac{n^3(n+1)^3}{R^4} + \frac{T \cdot t \cdot n^2(n+1)^2}{R^2}}{[(n+1)\rho_i + n \cdot \rho_o]R + n(n+1)\rho \cdot t}},$$

wherein E is average Young's modulus of sclera, T is tension of sclera, t is average thickness of sclera, R is average radius of eyeball, v is Poisson's ratio, $\rho_i$ is average density of inner eyeball, $\rho$ is average density of sclera, $\rho_o$ is air density, n is modal order number.

6. The acoustic wave intraocular pressure detecting device as claimed in claim 5, wherein $T=T_0+IOP\cdot R/2t$, the /OP is the intraocular pressure value, $T_0$ is an initial tension value that the eyeball is under a balanced status of inner pressure and outer pressure.

7. An acoustic wave intraocular pressure detecting method, comprising:
   generating a vibration wave to skin or bones using a driver, the vibration wave is transmitted to orbital bones via skin and bones to form a standing wave of the basin effect on an eyeball inside the orbital bones, wherein the standing wave vibrates the eyeball or cornea to generate an acoustic wave signal with a resonance frequency and emit the acoustic wave signal outwardly,
   positioning a receiver at a distance from the cornea or eyeball to receive the acoustic wave signal; and
   converting the acoustic wave signal into an intraocular pressure value.

8. The method as claimed in claim 7, further comprising:
   (S3) sending the intraocular pressure value to a database for comparison.

9. The method as claimed in claim 8, wherein energy of the vibration wave is greater than 1.23 mW.

10. The method as claimed in claim 8, wherein the vibration wave is a sinusoidal wave signal, frequency of the sinusoidal wave is about 0~1.0 kHz.

11. The method as claimed in claim 8, wherein the vibration wave is a pulse signal, frequency of the pulse signal is about 0~1.0 kHz, cycle of the pulse signal is about 10~20 seconds.

12. An acoustic wave intraocular pressure detecting method, comprising:
   using a driver to generate a vibration wave to skin or bones, the vibration wave is transmitted to orbital bones via skin and bones to form a standing wave of the basin effect on an eyeball inside the orbital bones, wherein the standing wave vibrates the eyeball or cornea to generate an acoustic wave signal with a resonance frequency and emit the acoustic wave signal outwardly,
   using a receiver to receive the acoustic wave signal and convert the acoustic wave signal into an intraocular pressure value; and
   sending the intraocular pressure value to a database for comparison;
   wherein the resonance frequency and the intraocular pressure value has a mathematical relationship:

$$f_n = \frac{1}{2\pi} \sqrt{\frac{\frac{(E+T) \cdot t^3}{12(1-v^2)} \frac{n^3(n+1)^3}{R^4} + \frac{T \cdot t \cdot n^2(n+1)^2}{R^2}}{[(n+1)\rho_i + n \cdot \rho_o]R + n(n+1)\rho \cdot t}},$$

wherein E is average Young's modulus of sclera, T is tension of sclera, t is average thickness of sclera, R is average radius of eyeball, v is Poisson's ratio, $\rho_i$ is average density of inner eyeball, $\rho$ is average density of sclera, $\rho_o$ is air density, n is modal order number.

13. The method as claimed in claim 12, wherein $T=T_0+IOP\cdot R/2t$, the IOP is the intraocular pressure value, $T_0$ is an initial tension value that the eyeball is under a balanced status of inner pressure and outer pressure.

* * * * *